(12) United States Patent
Otsuki et al.

(10) Patent No.: US 11,427,698 B2
(45) Date of Patent: Aug. 30, 2022

(54) RUBBER-METAL ADHESION PROMOTER, RUBBER COMPOSITION, AND TIRE

(71) Applicants: DIC Corporation, Tokyo (JP); National University Corporation, Iwate University, Morioka (JP)

(72) Inventors: Shujiro Otsuki, Ichihara (JP); Takayuki Odashima, Ichihara (JP); Hidetoshi Hirahara, Morioka (JP)

(73) Assignees: DIC Corporation, Tokyo (JP); National University Corporation, Iwate University, Morioka (JP)

( * ) Notice: Subject to any disclaimer, the term of this patent is extended or adjusted under 35 U.S.C. 154(b) by 0 days.

(21) Appl. No.: 16/549,201

(22) Filed: Aug. 23, 2019

(65) Prior Publication Data
US 2019/0375911 A1    Dec. 12, 2019

Related U.S. Application Data

(63) Continuation of application No. 15/507,848, filed as application No. PCT/JP2015/075592 on Sep. 9, 2015, now abandoned.

(30) Foreign Application Priority Data

Sep. 12, 2014   (JP) ............................. JP2014-187070

(51) Int. Cl.
| | |
|---|---|
| *C08K 5/098* | (2006.01) |
| *C08K 5/52* | (2006.01) |
| *C08K 5/55* | (2006.01) |
| *B60C 1/00* | (2006.01) |
| *B60C 9/00* | (2006.01) |
| *C07C 53/124* | (2006.01) |
| *C07C 53/128* | (2006.01) |

(52) U.S. Cl.
CPC ............... *C08K 5/098* (2013.01); *B60C 1/00* (2013.01); *B60C 9/0007* (2013.01); *C07C 53/124* (2013.01); *C07C 53/128* (2013.01); *C08K 5/52* (2013.01); *C08K 5/55* (2013.01)

(58) Field of Classification Search
None
See application file for complete search history.

(56) References Cited

U.S. PATENT DOCUMENTS

| | | |
|---|---|---|
| 3,296,242 A | 1/1967 | Turner et al. |
| 3,467,683 A | 9/1969 | Harson et al. |
| 3,839,246 A * | 10/1974 | Hamilton, Jr. .......... C08L 83/04 523/213 |
| 4,137,359 A | 1/1979 | Bak et al. |
| 4,234,496 A | 11/1980 | Harson |
| 4,341,842 A * | 7/1982 | Lampe ................. C09D 183/04 138/145 |
| 4,488,998 A | 12/1984 | Miller et al. |

(Continued)

FOREIGN PATENT DOCUMENTS

| | | |
|---|---|---|
| CN | 1745320 A | 3/2006 |
| CN | 101535204 A | 9/2009 |

(Continued)

OTHER PUBLICATIONS

International Search Report dated Dec. 22, 2015, issued for PCT/JP2015/075592 and English translation thereof.

(Continued)

*Primary Examiner* — Megan McCulley
(74) *Attorney, Agent, or Firm* — Locke Lord LLP; James E. Armstrong, IV; Nicholas J. DiCeglie, Jr.

(57) ABSTRACT

A rubber-metal adhesion promoter characterized by including: a metal salt (1) of a carboxylic acid which is a metal salt of an aliphatic carboxylic acid having 2 to 25 carbon atoms and in which the metal is bismuth, copper, antimony, silver or niobium; or a compound (2) represented by the following general formula (A): [wherein Z represents a structure selected from the following formulae (z-1) to (z-4); M represents bismuth, copper, antimony, silver or niobium; (RCOO) represents a residue of an aliphatic carboxylic acid having 2 to 25 carbon atoms; and x represents the valence of M minus 1].

[Chemical Formula 1]

$$[(RCOO)_xMO]_3Z \quad (A)$$

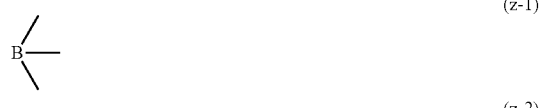

(z-1)

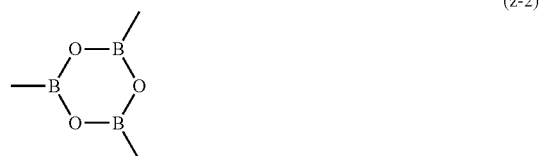

(z-2)

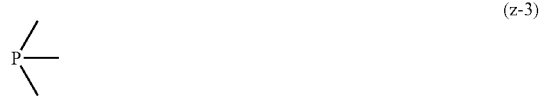

(z-3)

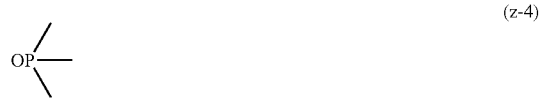

(z-4)

19 Claims, No Drawings

(56) References Cited

U.S. PATENT DOCUMENTS

| | | | |
|---|---|---|---|
| 4,589,804 A * | 5/1986 | Paeglis | C08L 23/26 156/308.4 |
| 4,609,499 A | 9/1986 | Esashi et al. | |
| 4,701,488 A | 10/1987 | Williams | |
| 4,719,266 A | 1/1988 | Craig | |
| 4,808,274 A | 2/1989 | Nguyen | |
| 5,098,946 A | 3/1992 | Kawazura et al. | |
| 5,244,955 A * | 9/1993 | Toyoda | C08K 3/22 524/397 |
| 5,276,172 A * | 1/1994 | Tate | C08J 5/10 556/28 |
| 5,391,627 A * | 2/1995 | Araki | C08K 5/098 474/202 |
| 6,207,752 B1 * | 3/2001 | Abraham | C08L 13/00 525/67 |
| 6,353,047 B1 | 3/2002 | Hilton et al. | |
| 10,450,439 B2 * | 10/2019 | Otsuki | B60C 9/0007 |
| 2002/0009608 A1 * | 1/2002 | Nishikawa | B60C 9/09 428/608 |
| 2003/0108664 A1 | 6/2003 | Kodas et al. | |
| 2007/0015893 A1 * | 1/2007 | Hakuta | C08F 210/18 528/34 |
| 2007/0191541 A1 | 8/2007 | Guennouni et al. | |
| 2008/0045664 A1 * | 2/2008 | Sone | C08C 19/25 525/271 |
| 2008/0188613 A1 * | 8/2008 | Tanaka | C08C 19/40 524/566 |
| 2010/0015416 A1 * | 1/2010 | Kawashima | C08K 3/10 428/195.1 |
| 2010/0173144 A1 * | 7/2010 | Schuette | C08G 18/664 428/304.4 |
| 2011/0023333 A1 * | 2/2011 | Schutte | C08G 18/10 36/32 R |
| 2011/0028598 A1 | 2/2011 | Veyland et al. | |
| 2011/0046263 A1 * | 2/2011 | Hoshino | C08L 15/00 523/152 |
| 2011/0129647 A1 * | 6/2011 | Duke, Jr. | C08G 18/4854 428/156 |
| 2011/0224364 A1 * | 9/2011 | Yamagishi | B60C 1/0016 524/571 |
| 2011/0290396 A1 * | 12/2011 | Nakagawa | C08L 15/00 152/450 |
| 2013/0324659 A1 * | 12/2013 | Shibata | C08L 15/00 524/526 |
| 2013/0345335 A1 * | 12/2013 | Shibata | C08K 5/098 523/156 |
| 2014/0228470 A1 * | 8/2014 | Molnar | C08K 5/1515 522/64 |
| 2016/0009971 A1 * | 1/2016 | Wang | C08G 18/44 428/314.4 |
| 2016/0237253 A1 * | 8/2016 | Kakubo | C08K 3/36 |

FOREIGN PATENT DOCUMENTS

| | | |
|---|---|---|
| CN | 101717582 A | 6/2010 |
| CN | 101986391 A | 3/2011 |
| CN | 102485331 A | 6/2012 |
| EP | 0466448 A1 | 1/1992 |
| EP | 0976784 A1 | 2/2000 |
| GB | 1258357 A | 12/1971 |
| JP | 49-039187 A | 10/1974 |
| JP | 55-017371 A | 2/1980 |
| JP | 59-179541 A | 10/1984 |
| JP | 59-223737 A | 12/1984 |
| JP | 60-109591 A | 6/1985 |
| JP | 60-158230 A | 8/1985 |
| JP | 62-283987 A | 12/1987 |
| JP | 63-289042 A | 11/1988 |
| JP | 03-192130 A | 8/1991 |
| JP | 04-230397 A | 8/1992 |
| JP | 06-329839 A | 11/1994 |
| JP | 07-011052 A | 1/1995 |
| JP | 07-109478 A | 4/1995 |
| JP | 2001-519435 A | 10/2001 |
| JP | 2004-359829 A | 12/2004 |
| JP | 2006-160826 A | 6/2006 |
| JP | 2006-291103 A | 10/2006 |
| JP | 2011-507999 A | 3/2011 |
| KR | 10-2001-0006557 A | 1/2001 |
| KR | 10-2001-0013421 A | 2/2001 |
| KR | 10-2001-0030938 A | 4/2001 |
| KR | 10-0416669 B1 | 4/2004 |
| KR | 10-2005-0051004 A | 6/2005 |
| WO | 1997/049776 A1 | 12/1997 |
| WO | 99/19336 A1 | 4/1999 |
| WO | 2010/031745 A1 | 3/2010 |
| WO | 2016/039376 A1 | 3/2016 |

OTHER PUBLICATIONS

Li Xiaoru et al., "Preparation and properties of nickel borate acylate", The Chinese Journal of Nonferrous Metals, vol. 11, No. 1, Feb. 2001, pp. 140-143. (English abstract is included.).

Office action dated Jan. 8, 2018, issued for the Chinese patent application No. 201580048181.8 and English translation thereof.

Supplementary European Search Report dated Apr. 5, 2018, issued for the European patent application No. 15839903.0.

Notification of the Second Office Action, issued in corresponding Chinese Patent Application No. CN 201580048181.8, dated Oct. 9, 2018.

Office Action dated Dec. 11, 2019, issued for the India Patent Application No. 201717006633.

Notice of Allowance issued in Japanese Patent Application No. JP 2016-547471, dated Dec. 1, 2020.

Notice of Allowance issued in Korean Patent Application No. KR 10-2017-7006200, dated Oct. 22, 2021.

* cited by examiner

RUBBER-METAL ADHESION PROMOTER, RUBBER COMPOSITION, AND TIRE

CROSS REFERENCE TO RELATED APPLICATIONS

This Application is a Continuation of U.S. patent application Ser. No. 15/507,848 filed on Mar. 1, 2017, which Application is a U.S. National Phase under 35 U.S.C. § 371 of International PCT Patent Application No. PCT/JP2015/075592, filed Sep. 9, 2015, which application claims priority to Japanese Patent Application No. 2014-187070 filed Sep. 12, 2014. The entire contents of these applications are incorporated herein by reference in their entireties.

TECHNICAL FIELD

The present invention relates to a rubber-metal adhesion promoter, and a rubber composition and a tire using the same. More specifically, the present invention relates to an adhesion promoter capable of exerting a high adhesive force between rubber and a metal, which is equivalent to or higher than that of a cobalt-containing adhesion promoter, without containing cobalt associated with concerns over toxicity; and a rubber composition and a tire using the same.

BACKGROUND ART

Conventionally, in order to enhance the performance of automobile tires, belt conveyors and the like, for example, steel cord or the like that is plated with brass has been used as a reinforcing material. In order to improve the adhesive force between the reinforcing material and natural rubber or synthetic rubber, the rubber contains an adhesion promoter. As the adhesion promoter, an organic acid cobalt metal soap (for example, cobalt stearate, cobalt naphthenate, cobalt tallate, cobalt boron metal soap, or the like) has been frequently used because of favorable adhesive properties with the steel cord and the rubber.

However, cobalt compounds such as the aforementioned organic acid cobalt metal soaps are listed in Group 2B which is said to be "possibly carcinogenic to humans" in the list of carcinogenic risks classified by the International Agency for Research on Cancer. In addition, since metallic cobalt which is a raw material of various cobalt compounds is a rare metal, its supply is unstable. As described above, cobalt compounds (organic acid cobalt metal soaps) using a raw material which is suspected to be carcinogenic and also unstable in supply tend to be avoided although adhesive properties with rubber and the metal (steel cord) are favorable, and there is a demand for alternative adhesion promoters (non-cobalt based adhesion promoters).

As a non-cobalt based adhesion promoter, for example, an adhesion promoter containing boron or phosphorus has been known. More specifically, for example, an adhesion promoter having a structure containing three atoms of nickel or bismuth bonded to boron or phosphorus via an oxygen atom and having both a residue of an aromatic carboxylic acid and a residue of an aliphatic carboxylic acid has been known (see, for example, Patent Document 1). However, the adhesion promoter disclosed in Patent Document 1 has a problem in that the adhesive force when adhering the rubber and the metal is not sufficient.

CITATION LIST

[Patent Document]
[Patent Document 1] Japanese Unexamined Patent Application, First Publication No. Hei 4-230397

SUMMARY OF INVENTION

Technical Problem

The problem to be solved by the present invention is to provide an adhesion promoter capable of exerting a high adhesive force between rubber and a metal than a cobalt-containing adhesion promoter without containing cobalt which is associated with concerns over toxicity; and a rubber composition and a tire using the same.

Solution to Problem

As a result of intensive investigations in order to solve the above problems, the present inventors have found the followings that led to the completion of the present invention: i.e., a metal salt of an aliphatic carboxylic acid having 2 to 25 carbon atoms in which the metal is bismuth, copper, antimony, silver or niobium becomes an adhesion promoter capable of exerting a high adhesive force between rubber and a metal, rather than a cobalt-containing adhesion promoter, without containing cobalt that is of concern for toxicity; and one having a specific structure containing any one of bismuth, copper, antimony, silver, or niobium which is bonded to boron or phosphorus via an oxygen atom, and having a residue of an aliphatic carboxylic acid in combination also becomes an adhesion promoter capable of exerting a high adhesive force between rubber and a metal, as compared with the one positively having an aromatic carboxylic acid residue as disclosed in the aforementioned Patent Document 1.

That is, the present invention includes the following aspects.

[1] A rubber-metal adhesion promoter characterized by including: a metal salt (1) of a carboxylic acid which is a metal salt of an aliphatic carboxylic acid having 2 to 25 carbon atoms and in which the metal is bismuth, copper, antimony, silver or niobium; or a compound (2) represented by the following general formula (A):

[Chemical Formula 1]

$$[(R\ COO)_xMO]_3Z \qquad (A)$$

[in the formula, Z represents a structure selected from the following formulae (z-1) to (z-4);

[Chemical Formula 2]

(z-1)

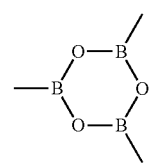

(z-2)

(z-3)

(z-4)

M represents bismuth, copper, antimony, silver or niobium; (RCOO) represents a residue of an aliphatic carboxylic acid having 2 to 25 carbon atoms; and x represents an integer of {(valence of M)−1}].

[2] The rubber-metal adhesion promoter according to the above [1], wherein the aforementioned metal salt (1) of the carboxylic acid is included, and the metal in the metal salt (1) of the carboxylic acid is bismuth or copper.

[3] The rubber-metal adhesion promoter according to the above [1] or [2], wherein the aforementioned metal salt (1) of the carboxylic acid is included, and the aliphatic carboxylic acid in the metal salt (1) of the carboxylic acid is an aliphatic monocarboxylic acid or an aliphatic dicarboxylic acid.

[4] The rubber-metal adhesion promoter according to the above [3], wherein the aliphatic carboxylic acid in the aforementioned metal salt (1) of the carboxylic acid is a saturated aliphatic monocarboxylic acid having 2 to 20 carbon atoms.

[5] The rubber-metal adhesion promoter according to the above [4], wherein the carboxylic acid in the aforementioned metal salt (1) of the carboxylic acid is 2-ethylhexanoic acid, neodecanoic acid, hexadecanoic acid or octadecanoic acid.

[6] The rubber-metal adhesion promoter according to the above [1], wherein the aforementioned compound (2) is included, and M in the compound (2) is bismuth or copper.

[7] The rubber-metal adhesion promoter according to the above [1] or [6], wherein the aforementioned compound (2) is included, and Z in the compound (2) is a structure represented by the aforementioned formula (z-1).

[8] The rubber-metal adhesion promoter according to the above [1], [6] or [7], wherein the aforementioned compound (2) is included, and (RCOO) in the compound (2) is a residue of a saturated aliphatic monocarboxylic acid having 2 to 20 carbon atoms.

[9] The rubber-metal adhesion promoter according to the above [8], wherein (RCOO) in the aforementioned compound (2) is a residue of 2-ethylhexanoic acid, a residue of neodecanoic acid, a residue of hexadecanoic acid or a residue of octadecanoic acid.

[10] The rubber-metal adhesion promoter according to any one of the above [1] to [9], which is used for adhering rubber and a steel cord.

[11] A rubber composition characterized by including: the rubber-metal adhesion promoter according to any one of the above [1] to [10]; and a rubber component.

[12] The rubber composition according to the above [11], which contains 0.01 to 10 parts by mass of the aforementioned rubber-metal adhesion promoter with respect to 100 parts by mass of the aforementioned rubber component.

[13] A tire characterized by having a steel cord/rubber composite including the rubber composition according to the above [11] or [12] and a steel cord.

Advantageous Effects of Invention

The rubber-metal adhesion promoter of the present invention is, despite being a non-cobalt based promoter, capable of exerting a higher adhesive force between rubber and a metal than a cobalt-containing adhesion promoter, especially even under wet heat conditions. By using the adhesion promoter of the present invention, it is possible to easily obtain a rubber composition capable of suitably producing automobile tires, belt conveyors and the like exhibiting strong adhesion between the steel cord and the rubber.

DESCRIPTION OF EMBODIMENTS

A rubber-metal adhesion promoter of the present invention is characterized by containing a metal salt (1) or a compound (2) as described above. Hereinafter, the metal salt (1) will be described in detail.

The metal salt (1) of a carboxylic acid in the present invention is a metal salt of an aliphatic carboxylic acid having 2 to 25 carbon atoms. Here, the metal species is bismuth, copper, antimony, silver or niobium. Among the metal species, bismuth, copper, antimony or silver is preferable, and bismuth or copper is more preferable, since an adhesion promoter capable of achieving a favorable adhesion between the steel cord and the rubber even under wet heat conditions is obtained.

In the present invention, when an aliphatic carboxylic acid having less than 2 carbon atoms is used, it is not preferable because it is difficult to form an adhesion promoter excellent in compatibility with the rubber, and as a result, it becomes difficult to obtain an adhesion promoter that exerts a high adhesive force between the rubber and the metal. In addition, when a carboxylic acid having more than 25 carbon atoms is used, it is not preferable because it is difficult to synthesize the metal salt (1), and as a result, it becomes difficult to obtain an adhesion promoter that exerts a high adhesive force between the rubber and the metal.

As the aliphatic carboxylic acid having 2 to 25 carbon atoms, for example, an aliphatic monocarboxylic acid and an aliphatic dicarboxylic acid can be preferably exemplified. Here, in the present invention, the number of carbon atoms of the aliphatic carboxylic acid refers to the number of carbon atoms including those of the carboxyl group.

Examples of the aliphatic carboxylic acid having 2 to 25 carbon atoms include saturated aliphatic monocarboxylic acids and unsaturated aliphatic monocarboxylic acids. Examples of the saturated aliphatic monocarboxylic acid include ethanoic acid, propanoic acid, butanoic acid, pentanoic acid, hexanoic acid, 2-ethylhexanoic acid, heptanoic acid, octanoic acid, nonanoic acid, isononanoic acid, decanoic acid, neodecanoic acid, dodecanoic acid, tetradecanoic acid, hexadecanoic acid, heptadecanoic acid, octadecanoic acid, eicosanoic acid, docosanoic acid, tetracosanoic acid and naphthenic acid.

Examples of the unsaturated aliphatic monocarboxylic acid include 9-hexadecenoic acid, cis-9-octadecenoic acid, 11-octadecenoic acid, cis, cis-9,12-octadecadienoic acid, 9,12,15-octadecatrienoic acid, 6,9,12-octadecatrienoic acid, 9,11,13-octadecatrienoic acid, eicosanoic acid, 8,11-eicosadienoic acid, 5,8,11-eicosatrienoic acid, 5,8,11,14-eicosatetraenoic acid, tung oil acid, linseed oil acid, soybean oil acid, resin acid, tall oil fatty acid, rosin acid, abietic acid, neoabietic acid, palustric acid, pimaric acid and dehydroabietic acid.

Examples of the aliphatic dicarboxylic acid having 2 to 25 carbon atoms include saturated aliphatic dicarboxylic acids and unsaturated aliphatic dicarboxylic acids. Examples of the saturated aliphatic dicarboxylic acid include oxalic acid, malonic acid, succinic acid, glutaric acid and adipic acid.

Examples of the unsaturated aliphatic dicarboxylic acid include fumaric acid and maleic acid.

Among the aforementioned carboxylic acids, saturated aliphatic monocarboxylic acids are preferable because they hardly affect adversely the sulfur crosslinking of the rubber, and as a result, a rubber cured product having less adverse effects on the rubber physical properties which is used for automobile tires, belt conveyors and the like can be obtained. Among the saturated fatty acids, a saturated aliphatic monocarboxylic acid having 2 to 20 carbon atoms is preferable, and 2-ethylhexanoic acid, neodecanoic acid, hexadecanoic acid or octadecanoic acid is more preferable.

The metal salt (1) of a carboxylic acid in the present invention can be obtained, for example, by the following method.

Production Method 1: A production method in which an aliphatic carboxylic acid (a) having 2 to 25 carbon atoms is directly reacted with at least one selected from an oxide (b-1) of a metal (bismuth, copper, antimony, silver or niobium), a hydroxide (b-2) of a metal (bismuth, copper, antimony, silver or niobium) and a carbonate (b-3) of a metal (bismuth, copper, antimony, silver or niobium) (direct method).

Production Method 2: A production method in which, after reacting an aliphatic carboxylic acid (a) having 2 to 25 carbon atoms with sodium hydroxide in the presence of water to obtain a sodium salt of an aliphatic carboxylic acid, the sodium salt of the aliphatic carboxylic acid is reacted with at least one selected from a sulfate (c-1) of a metal (bismuth, copper, antimony, silver or niobium), a chloride (c-2) of a metal (bismuth, copper, antimony, silver or niobium) and a nitrate (c-3) of a metal (bismuth, copper, antimony, silver or niobium) (double decomposition method).

Examples of the oxide (b-1) of the metal (bismuth, copper, antimony, silver or niobium) used in the above Production Method 1 include bismuth(III) oxide, copper(I) oxide, copper(II) oxide, antimony(III) oxide, antimony(V) oxide, silver(I) oxide, silver(II) oxide, silver(III) oxide, niobium(IV) oxide and niobium(V) oxide. Examples of the hydroxide (b-2) of the metal (bismuth, copper, antimony, silver or niobium) include copper(II) hydroxide and the like. Examples of the carbonate (b-3) of the metal (bismuth, copper, antimony, silver or niobium) include bismuth(III) carbonate, bismuth(III) subcarbonate and copper(II) carbonate.

Examples of the sulfate (c-1) of the metal (bismuth, copper, antimony, silver or niobium) used in the above Production Method 2 include copper(II) sulfate and the like. Examples of the chloride (c-2) of the metal (bismuth, copper, antimony, silver or niobium) include bismuth(III) oxychloride, copper(I) chloride, copper(II) chloride, antimony(III) chloride, antimony(V) chloride, silver(I) chloride and niobium(V) chloride. Examples of the nitrate (c-3) of the metal (bismuth, copper, antimony, silver or niobium) include bismuth(III) nitrate, bismuth(III) subnitrate and silver(I) nitrate.

In the above Production Method 1, the reaction temperature at the time of reacting the aliphatic carboxylic acid (a) having 2 to 25 carbon atoms with the compounds (b-1) to (b-3) is usually from 50 to 150° C. In addition, the reaction time is usually from 1 to 20 hours.

In the above Production Method 2, the reaction temperature at the time of reacting the aliphatic carboxylic acid (a) having 2 to 25 carbon atoms with sodium hydroxide in the presence of an organic solvent is usually from 20 to 100° C. In addition, the reaction time is usually from 1 to 5 hours.

In the above Production Method 2, the reaction temperature at the time of reacting the sodium salt of an aliphatic carboxylic acid with the compounds (c-1) to (c-3) is usually from 20 to 100° C. In addition, the reaction time is usually from 1 to 5 hours.

In the Production Method 2, after reacting the sodium salt of the aliphatic carboxylic acid with the compounds (c-1) to (c-3), an aqueous layer in the reaction system is separated. Thereafter, by removing the solvent present in the oil layer by distillation under reduced pressure, the rubber-metal adhesion promoter (fatty acid metal salt) of the present invention can be obtained.

Next, the compound (2) represented by the general formula (A) in the present invention will be described in detail. (RCOO) in the compound (2) represents a residue of an aliphatic carboxylic acid having 2 to 25 carbon atoms. The residue of an aliphatic carboxylic acid having less than 2 carbon atoms is unlikely to become an adhesion promoter excellent in compatibility with the rubber, and as a result, it becomes difficult to obtain an adhesion promoter that exerts high adhesive force between the rubber and the metal, and is therefore not preferable. In addition, not only it is difficult to synthesize the compound (2) with the residue of a carboxylic acid having more than 25 carbon atoms, but also it is difficult to disperse in the rubber or adsorb to the surface of the steel cord. As a result, it becomes difficult to obtain an adhesion promoter that exerts high adhesive force between the rubber and the metal, and is therefore not preferable. Here, in the present invention, the number of carbon atoms of (RCOO) refers to the number of carbon atoms including those of the carboxyl group.

As the residue of the aliphatic monocarboxylic acid having 2 to 25 carbon atoms, for example, a residue of an aliphatic monocarboxylic acid can be preferably exemplified. As these residues, for example, a residue derived from the aliphatic monocarboxylic acid described above can be preferably exemplified.

Among the residues of the aliphatic carboxylic acid, the residues of a saturated aliphatic monocarboxylic acid is preferred since it does not crosslink with the rubber and can further develop the performance as the adhesion promoter by further promoting dispersion in the vicinity of the steel cord or adsorption to the surface of the steel cord. Among the residues of a saturated aliphatic monocarboxylic acid, a residue of a saturated aliphatic monocarboxylic acid having 2 to 20 carbon atoms is preferable, and a residue of 2-ethylhexanoic acid, a residue of neodecanoic acid, a residue of hexadecanoic acid or a residue of octadecanoic acid is more preferable.

M in the compound represented by the general formula (A) is a metal species, and more specifically, is bismuth, copper, antimony, silver or niobium. Among the metal species, bismuth, copper, antimony or silver is preferable, and bismuth or copper is more preferable, since an adhesion promoter capable of achieving a favorable adhesion between the steel cord and the rubber even under wet heat conditions is obtained.

Further, x in the compound (2) represented by the general formula (A) is an integer of {(valence of M)−1}.

Z in the compound (2) represented by the general formula (A) is a structure selected from the following formulae (z-1) to (z-4).

[Chemical Formula 3]

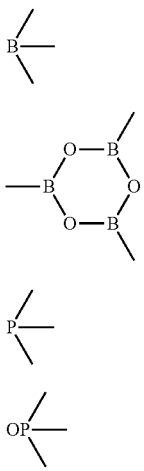

Among the above structures, the structure represented by the above formula (z-1) is preferable because it is easy to obtain an adhesion promoter that exerts high adhesive force between the rubber and the metal.

For example, the compound (2) represented by the general formula (A) can be produced by a method of mixing and heating an aliphatic carboxylic acid (a) having 2 to 25 carbon atoms; a boric acid ester (d-1) of a lower alcohol having 1 to 5 carbon atoms, a metaboric acid ester (d-2) of a lower alcohol having 1 to 5 carbon atoms, a phosphoric acid ester (d-3) of a lower alcohol having 1 to 5 carbon atoms or a phosphite ester (d-4) of a lower alcohol having 1 to 5 carbon atoms; an acid (e) capable of forming a volatile ester with a lower alcohol residue of 1 to 5 carbon atoms present in the esters (d-1) to (d-4); and a metal compound M (1) as a metal source, and removing the resulting volatile ester.

As the monocarboxylic acid (a), for example, the aforementioned aliphatic monocarboxylic acids having 2 to 25 carbon atoms and the like can be mentioned.

Examples of the boric acid ester (d-1) of a lower alcohol include trimethyl borate, triethyl borate, tripropyl borate and tributyl borate. Examples of the metaboric acid ester (d-2) of a lower alcohol include trimethyl metaborate, triethyl metaborate, tripropyl metaborate and tributyl metaborate. Examples of the phosphoric acid ester (d-3) of a lower alcohol include methyl phosphate, ethyl phosphate, propyl phosphate and butyl phosphate. Examples of the phosphite ester (d-4) of a lower alcohol include methyl phosphite, ethyl phosphite, propyl phosphite and butyl phosphite.

As the metal compound M (f) serving as the metal source, for example, the oxide (b-1), the hydroxide (b-2), the carbonate (b-3) and the like described above can be used.

Examples of the acid (e) include ethanoic acid, propanoic acid and butanoic acid.

The proportion of the metal compound M (f) used as the metal source is, for example, from 20 to 100 parts by mass per 100 parts by mass of the aliphatic carboxylic acid (a) having 2 to 25 carbon atoms. In addition, the proportion of the above (d) used is, for example, from 10 to 50 parts by mass per 100 parts by mass of the aliphatic carboxylic acid (a) having 2 to 25 carbon atoms. Further, the proportion of the acid (e) used is, for example, from 10 to 50 parts by mass per 100 parts by mass of the aliphatic carboxylic acid (a) having 2 to 25 carbon atoms.

Among the above production methods, the production method including a first step of mixing and heating an aliphatic carboxylic acid (a) having 2 to 25 carbon atoms, an acid (e) capable of forming a volatile ester with a lower alcohol residue of 1 to 5 carbon atoms present in the ester (d) and a metal compound M (f) as a metal source to obtain a reaction product; followed by a second step of adding, after removing water from the reaction system containing the reaction product, the aforementioned esters (d-1) to (d-4) to the reaction system from which the water has been removed, and allowing the reaction product to react with the esters (d-1) to (d-4) reactant, is preferable because it is possible to prevent the hydrolysis of the esters (d-1) to (d-4) by the water produced in the first step, and as a result, it is possible to efficiently produce the compound (2) in the present invention.

In the above production method, the temperature for reacting the aliphatic carboxylic acid (a) having 2 to 25 carbon atoms, the esters (d-1) to (d-4), the acid (e) and the metal compound M (f) is, for example, from 100 to 250° C., and preferably from 150 to 220° C. In addition, the reaction time is, for example, from 1 to 20 hours, and preferably from 1 to 5 hours.

The rubber composition of the present invention is characterized by containing the adhesion promoter of the present invention and a rubber component. As the rubber component, for example, diene-based rubber can be used. Examples of the diene-based rubber include natural rubber (NR) and diene-based synthetic rubber. Examples of the diene-based synthetic rubber include isoprene rubber (IR), butadiene rubber (BR), styrene butadiene rubber (SBR), styrene isoprene butadiene rubber (SIBR), ethylene propylene diene rubber (EPDM), chloroprene rubber (CR) and acrylonitrile butadiene rubber (NBR). Among these rubber components, NR which is easy to elongate and crystallize and excellent in fracture properties is preferable.

In the rubber composition according to the present invention, a filler such as carbon black or silica can be blended as a reinforcing agent.

The carbon black is not particularly limited, and for example, carbon black of SAF, ISAF, HAF or FEF type can be used, and two or more types of these may be used in combination. The amount of the carbon black added is not particularly limited, but it is preferably from 20 to 100 parts by mass, and more preferably from 40 to 80 parts by mass with respect to 100 parts by mass of the diene-based rubber.

Examples of the silica include wet silica (hydrous silicic acid), dry silica (anhydrous silicic acid) and surface treated silica. In the case of adding silica, the added amount thereof is not particularly limited, but it is preferably 0 parts by mass or more and 40 parts by mass or less, and more preferably 0.1 parts by mass or more and 20 parts by mass or less, with respect to 100 parts by mass of the diene-based rubber.

Sulfur as a vulcanizing agent is usually added to the rubber composition according to the present invention. The added amount of sulfur is preferably from 1 to 10 parts by mass, and more preferably from 2 to 8 parts by mass with respect to 100 parts by mass of the diene-based rubber. Examples of sulfur include powdered sulfur, precipitated sulfur, colloidal sulfur, insoluble sulfur and oil-treated sulfur, and are not particularly limited.

A vulcanization accelerator can be added to the rubber composition of the present invention. As the vulcanization accelerator, for example, a sulfenamide-based vulcanization accelerator can be mentioned. Here, examples of the sulfenamide vulcanization accelerator include N-cyclohexyl-2-benzothiazole sulfenamide (CZ, JIS abbreviation: CBS), N-tert-butyl-2-benzothiazole sulfenamide (NS, JIS Abbreviation: BBS), N-oxydiethylene-2-benzothiazole sulfenamide (OBS), N,N-diisopropyl-2-benzothiazole sulfenamide (DPBS) and N,N-dicyclohexyl-2-benzothiazole sulfenamide (DZ, JIS abbreviation: DCBS).

The content of the vulcanization accelerator is preferably from 1 to 12 parts by mass, more preferably from 2 to 10 parts by mass, and even more preferably from 3 to 9 parts by mass, with respect to 100 parts by mass of the rubber component.

In addition to the above components, various compounding agents can be arbitrarily added to the rubber composition according to the present invention. Examples of such compounding agents include stearic acid, wax, oil, antioxidants and processing aids.

The rubber composition of the present invention can be prepared by kneading using a mixer such as a Banbury mixer or a kneader that is commonly used.

The rubber composition of the present invention can be suitably used, in particular, as a rubber composition for covering various steel cords. In particular, it is preferably used as a rubber composition for covering (topping) a steel cord used as a reinforcing material for a pneumatic tire such as a belt layer, a carcass layer, a chafer layer and the like, and a steel cord topping sheet is produced by a topping device such as a steel calender in accordance with a conventional method and this is used as a tire reinforcing member and molded and vulcanized in accordance with a conventional method, thereby a tire having a steel cord/rubber composite can be produced.

The content of the rubber-metal adhesion promoter according to the present invention in the rubber composition of the present invention is preferably from 0.01 to 10 parts by mass, and more preferably from 1 to 6 parts by mass, with respect to 100 parts by mass of the rubber component.

EXAMPLES

Hereinafter, the present invention will be described in detail by referring to Examples of the present invention and comparing them with Comparative Examples. In the Examples and Comparative Examples, unless stated otherwise, "parts" and "%" refer to mass-referenced values.

Synthesis Example 1 [Adhesion Promoter (1-1): Synthesis of Metal Salt (1-1)]

400 g of 2-ethylhexanoic acid and 134 g of antimony(III) oxide were charged into a flask, and the resulting mixture was heated and stirred at 120° C. for 2 hours. Then, the resultant was dried under reduced pressure at 120° C. for 1 hour to obtain a metal salt (1-1) used in the present invention. It should be noted that the metal salt (1-1) can also be said to be an adhesion promoter (1-1) of the present invention containing the metal salt (1-1).

Synthesis Example 2 (Adhesion Promoter (1-2): Synthesis of Metal Salt (1-2))

A metal salt (1-2) used in the present invention was obtained in the same manner as in Synthesis Example 1 except that 483 g of neodecanoic acid was used in place of 400 g of 2-ethylhexanoic acid. It should be noted that the metal salt (1-2) can also be said to be an adhesion promoter (1-2) of the present invention containing the metal salt (1-2).

Synthesis Example 3 (Adhesion Promoter (1-3): Synthesis of Metal Salt (1-3))

483 g of neodecanoic acid and 43 g of niobium(II) oxide were charged into a flask, and the resulting mixture was heated and stirred at 120° C. for 2 hours. Then, the resultant was dried under reduced pressure at 120° C. for 1 hour to obtain a metal salt (1-3) used in the present invention. It should be noted that the metal salt (1-3) can also be said to be an adhesion promoter (1-3) of the present invention containing the metal salt (1-3).

Synthesis Example 4 [Adhesion Promoter (2-1): Synthesis of Compound (2-1)]

233 g of bismuth(III) oxide was added to a mixed acid of 63 g of acetic acid and 342 g of neodecanoic acid, and then the resulting mixture was heated and stirred at 120° C. for 2 hours. Then, after drying the resultant under reduced pressure at 120° C. for 1 hour, 80 g of tributyl borate was reacted with the produced bismuth metal salt, and butyl acetate produced as a by-product was distilled off to obtain a compound (2-1) used in the present invention. It should be noted that the compound (2-1) can also be said to be an adhesion promoter (2-1) of the present invention containing the compound (2-1).

Synthesis Example 5 (Adhesion Promoter (2-2): Synthesis of Compound (2-2))

A compound (2-2) used in the present invention was obtained in the same manner as in Synthesis Example 4 except that 80 g of copper(II) oxide was used in place of 233 g of bismuth(III) oxide. It should be noted that the compound (2-2) can also be said to be an adhesion promoter (2-2) of the present invention containing the compound (2-2).

Synthesis Example 6 (Adhesion Promoter (2-3): Synthesis of Compound (2-3))

A compound (2-3) used in the present invention was obtained in the same manner as in Synthesis Example 4 except that 146 g of antimony(III) oxide was used in place of 233 g of bismuth(III) oxide. It should be noted that the compound (2-3) can also be said to be an adhesion promoter (2-3) of the present invention containing the compound (2-3).

Synthesis Example 7 (Adhesion Promoter (2-4): Synthesis of Compound (2-4))

A compound (2-4) used in the present invention was obtained in the same manner as in Synthesis Example 4 except that 124 g of silver(II) oxide was used in place of 233 g of bismuth(III) oxide. It should be noted that the compound (2-4) can also be said to be an adhesion promoter (2-4) of the present invention containing the compound (2-4).

Synthesis Example 8 (Adhesion Promoter (2-5): Synthesis of Compound (2-5))

A compound (2-5) used in the present invention was obtained in the same manner as in Experimental Example 4 except that 125 g of niobium(IV) oxide was used in place of 233 g of bismuth(III) oxide. It should be noted that the compound (2-5) can also be said to be an adhesion promoter (2-5) of the present invention containing the compound (2-5).

Comparative Synthesis Example 1 [Adhesion Promoter (2'-1): Synthesis of Comparative Compound (2'-1)]

210 g of neodecanoic acid, 147 g of propionic acid and 300 g of xylene were charged into a reaction flask and heated to 50° C. with mechanical stirring. 171 g of cobalt(II) hydroxide was added thereto, and the temperature was raised to 90° C. with mechanical stirring to produce a mobile blue liquid. Further, heat was applied and the reaction water was removed by xylene loading using a Dean & Stark trap. After the temperature reached 140° C., 73 g of benzoic acid dissolved in 150 g of xylene was gradually added to the reaction mixture, and the produced water was continuously removed.

After completion of the water removal, xylene was removed by short path distillation to a maximum temperature of 155° C., and a vacuum was applied to complete the removal. 138 g of tributyl borate was added thereto. The reaction mixture was heated to 190° C. and refluxed for 3 hours. 220 g of n-butyl propionate was then removed by distillation at the maximum temperature of 220° C., and a vacuum was applied to complete the ester removal to obtain a comparative compound (2'-1).

The comparative compound (2'-1) was a hard blue solid represented by the following formula:

B(OCoOCOB')(OCoOCOA')$_2$

[In the formula, OCOA' is a neodecanoic acid ester, and OCOB' is a benzoic acid ester]. It should be noted that the comparative compound (2'-1) can also be said to be a comparative adhesion promoter (2'-1) containing the comparative compound (2'-1).

Example 1 (Preparation of Rubber Composition of the Present Invention)

100 parts of natural rubber (grade: RSS 1), 4 parts of the adhesion promoter (1-1), 50 parts of carbon black (SEAST G-S manufactured by Tokai Carbon Co., Ltd.), 5 parts of oil (Dutrex R manufactured by Shell Chemicals Japan Ltd.), 8 parts of zinc white, 1 part of an antioxidant (Nocrac 810NA manufactured by Ouchi Shinko Chemical Industrial Co., Ltd.), 5 parts of insoluble sulfur, 2 parts of stearic acid and 0.5 parts of a vulcanization accelerator (Nocceler CZ, manufactured by Ouchi Shinko Chemical Industrial Co., Ltd.) were kneaded at 40° C. to obtain a rubber composition (1) of the present invention. A cured product (test piece) of a rubber composition in which a steel cord was sandwiched was prepared using the obtained rubber composition (1), and the adhesive properties between the steel cord and rubber were evaluated. The method for preparing a test piece and the method for evaluating the adhesive properties are shown below. In addition, the evaluation results are shown in Table 1.

<Method for Preparing Test Piece>

The rubber composition (1) was subjected to a heat treatment by a double test roller to prepare a rubber sheet having a width of 100 mm, a thickness of 6 mm and a length of 100 mm. Two rubber pieces having a width of 10 mm, a thickness of 6 mm and a length of 60 mm were cut out from the rubber sheet. A 1×4×0.25 mm steel cord plated with brass (Cu 65%, Zn 35%) was sandwiched between the aforementioned two rubber pieces and vulcanized at 160° C. for 10 minutes to prepare a rubber composition test piece to which the steel cord was adhered.

<Evaluation Method of Adhesive Properties>

A pulling test was conducted by a method in accordance with ASTM D2229 using the aforementioned test piece, and the adhesive force between the rubber and the steel cord was measured. For the measurement of the adhesive force, the following three types of measurements were carried out.

Initial adhesive force: A test piece was prepared by vulcanization under the above vulcanization conditions, and measurements were conducted after 24 hours.

Adhesive force after hygrothermal aging test: The test piece vulcanized under the above vulcanization conditions was subjected to water immersion aging by being immersed in hot water at 90° C. for 72 hours, and then the adhesive force was measured.

Adhesive force after heat aging test: The test piece vulcanized under the above vulcanization conditions was left to stand at 110° C. for 72 hours to measure the adhesive force.

It should be noted that the measured values of the above three adhesive forces are relative adhesive force values when the adhesive forces of a comparative metal salt (1'-2) described later are taken as 100.

Examples 2 to 15

Rubber compositions (1) to (15) were obtained in the same manner as in Example 1 except that the metal salts (1-1) to (1-10) or the compounds (2-1) to (2-5) [adhesion promoters of the present invention] shown in Table 1 were used. An evaluation test of adhesive properties was carried out in the same manner as in Example 1, and the results are shown in Table 1. It should be noted that in Examples 2 to 15, the amounts of the respective metal salts (1-1) to (1-10) or the compounds (2-1) to (2-5) used were added so that the metal molar concentrations in the rubber compositions were the same.

TABLE 1

| | Metal Salt (1) or Compound (2) (Adhesion Promoter) | | | | | Adhesion after aging test | |
|---|---|---|---|---|---|---|---|
| | Metal Salt or Compound | Synthesis Example | Metal salt name or compound name | Amount used (parts) | Initial Adhesion | Adhesion after hygrothermal aging test | Adhesion after heat aging test |
| Ex. 1 | (1-1) | Synthesis Example 1 | Antimony(III) 2-ethylhexanoate | 4.0 | 110 | 105 | 120 |
| Ex. 2 | (1-2) | Synthesis Example 2 | Antimony(III) neodecanoate | 4.7 | 108 | 110 | 115 |
| Ex. 3 | (1-3) | Synthesis Example 3 | Niobium(IV) neodecanoate | 5.7 | 101 | 105 | 102 |
| Ex. 4 | (1-4) | | Bismuth(III) 2-ethylhexanoate | 4.7 | 128 | 114 | 120 |

TABLE 1-continued

| | Metal Salt (1) or Compound (2) (Adhesion Promoter) | | | | Initial Adhesion | Adhesion after aging test | |
|---|---|---|---|---|---|---|---|
| | | | | | | Adhesion after | |
| | Metal Salt or Compound | Synthesis Example | Metal salt name or compound name | Amount used (parts) | | hygrothermal aging test | Adhesion after heat aging test |
| Ex. 5 | (1-5) | | Copper(II) 2-ethylhexanoate | 3.0 | 122 | 115 | 144 |
| Ex. 6 | (1-6) | | Silver(I) 2-ethylhexanoate | 1.8 | 108 | 110 | 112 |
| Ex. 7 | (1-7) | | Niobium(IV) 2-ethylhexanoate | 4.8 | 103 | 110 | 108 |
| Ex. 8 | (1-8) | | Bismuth(III) neodecanoate | 5.4 | 125 | 120 | 125 |
| Ex. 9 | (1-9) | | Copper(II) neodecanoate | 3.5 | 120 | 118 | 122 |
| Ex. 10 | (1-10) | | Silver(II) neodecanoate | 3.3 | 104 | 108 | 110 |
| Ex. 11 | (2-1) | Synthesis Example 4 | Bismuth(III) boron neodecanoate | 4.2 | 122 | 120 | 130 |
| Ex. 12 | (2-2) | Synthesis Example 5 | Copper(II) boron neodecanoate | 2.2 | 115 | 125 | 128 |
| Ex. 13 | (2-3) | Synthesis Example 6 | Antimony(III) boron neodecanoate | 3.5 | 112 | 120 | 125 |
| Ex. 14 | (2-4) | Synthesis Example 7 | Silver(II) boron neodecanoate | 2.2 | 105 | 120 | 120 |
| Ex. 15 | (2-5) | Synthesis Example 8 | Niobium(IV) boron neodecanoate | 4.6 | 102 | 118 | 110 |

Comparative Examples 1 to 12 (Preparation of Comparative Rubber Compositions)

Comparative rubber compositions (1') to (12') were obtained in the same manner as in Example 1 except that the metal salts (1'-2) to (1'-11) or the compound (2'-1) [comparative adhesion promoters] and the compound (2'-2) shown in Table 2 were used. An evaluation test of adhesive properties was carried out in the same manner as in Example 1, and the results are shown in Table 2. It should be noted that in Comparative Examples 1 to 12, the amounts of the respective metal salts (1'-2) to (1'-11) or the compounds (2'-1) to (2'-2) used were added so that the metal molar concentrations in the rubber compositions were the same.

TABLE 2

| | Metal Salt (1') or Compound (2') (Adhesion Promoter) | | | | Initial Adhesion | Adhesion after aging test | |
|---|---|---|---|---|---|---|---|
| | | | | | | Adhesion after | |
| | Metal Salt or Compound | Synthesis Example | Metal salt name or compound name | Amount used (parts) | | hygrothermal aging test | Adhesion after heat aging test |
| Comp. Ex. 1 | (1'-2) | | Cobalt(II) 2-ethylhexanoate | 2.7 | 100 | 100 | 100 |
| Comp. Ex. 2 | (1'-3) | | Iron(II) 2-ethylhexanoate | 3.8 | 25 | 25 | 20 |
| Comp. Ex. 3 | (1'-4) | | Manganese(II) 2-ethylhexanoate | 2.9 | 24 | 27 | 18 |
| Comp. Ex. 4 | (1'-5) | | Yttrium(II) 2-ethylhexanoate | 3.7 | 24 | 26 | 16 |
| Comp. Ex. 5 | (1'-6) | | Magnesium(II) 2-ethylhexanoate | 3.2 | 23 | 27 | 20 |
| Comp. Ex. 6 | (1'-7) | | Zinc(II) 2-ethylhexanoate | 2.1 | 21 | 22 | 17 |
| Comp. Ex. 7 | (1'-8) | | Lead(II) 2-ethylhexanoate | 4.0 | 19 | 22 | 18 |
| Comp. Ex. 8 | (1'-9) | | Strontium(II) 2-ethylhexanoate | 3.9 | 12 | 16 | 10 |
| Comp. Ex. 9 | (1'-10) | | Calcium(II) 2-ethylhexanoate | 3.4 | 10 | 12 | 10 |
| Comp. Ex. 10 | (1'-11) | | Barium(II) 2-ethylhexanoate | 4.6 | 7 | 10 | 5 |
| Comp. Ex. 11 | (2'-1) | Comparative Synthesis Example 1 | Cobalt(II) boron (neodecanoate + benzoate) | 3.3 | 75 | 80 | 80 |
| Comp. Ex. 12 | (2'-2) | | Cobalt(II) boron neodecanoate | 1.9 | 100 | 102 | 101 |

INDUSTRIAL APPLICABILITY

The present invention is used, for example, in automobile tires, belt conveyors and the like in order to promote adhesion between rubber and a metal to enhance the performance.

The invention claimed is:

1. A method of adhering rubber and metal comprising applying a rubber composition comprising a rubber-metal adhesion promoter and a rubber component to a metal component and vulcanizing the rubber to adhere the rubber component and the metal component;
   wherein the rubber-metal adhesion promoter comprises:
   a metal salt (1) of a carboxylic acid which is a metal salt of an aliphatic carboxylic acid having 2 to 25 carbon atoms and in which the metal is bismuth; and the rubber component is one or more selected from the group consisting of natural rubber (NR), isoprene rubber (IR), butadiene rubber (BR), styrene butadiene rubber (SBR), styrene isoprene butadiene rubber (SIBR), chloroprene rubber (CR) and acrylonitrile butadiene rubber (NBR); and
   the rubber composition comprises 0 parts by mass of silica with respect to 100 parts by mass of the rubber component.

2. The method of adhering rubber and metal according to claim 1,
   wherein the aliphatic carboxylic acid in the metal salt (1) of the carboxylic acid is an aliphatic monocarboxylic acid or an aliphatic dicarboxylic acid.

3. The method of adhering rubber and metal according to claim 2,
   wherein the aliphatic carboxylic acid in said metal salt (1) of the carboxylic acid is a saturated aliphatic monocarboxylic acid having 2 to 20 carbon atoms.

4. The method of adhering rubber and metal according to claim 3,
   wherein the carboxylic acid in said metal salt (1) of the carboxylic acid is 2-ethylhexanoic acid, neodecanoic acid, hexadecanoic acid or octadecanoic acid.

5. The method of adhering rubber and metal according to claim 1, wherein the metal component is a steel cord.

6. The method of adhering rubber and metal according to claim 1, wherein the amount of rubber-adhesion promoter is 0.01 to 10 parts by mass with respect to 100 parts by mass of said rubber component.

7. A method of producing a rubber composition for use in tires and belt conveyors comprising adding a rubber-metal adhesion promoter to a rubber component to produce the rubber composition;
wherein the rubber-metal adhesion promoter comprises:
a metal salt (1) of a carboxylic acid which is a metal salt of an aliphatic carboxylic acid having 2 to 25 carbon atoms and in which the metal is bismuth; and
the rubber component is one or more selected from the group consisting of natural rubber (NR), isoprene rubber (IR), butadiene rubber (BR), styrene butadiene rubber (SBR), styrene isoprene butadiene rubber (SIBR), chloroprene rubber (CR) and acrylonitrile butadiene rubber (NBR) ; and
the rubber composition comprises 0 parts by mass of silica with respect to 100 parts by mass of the rubber component.

8. The method of producing the rubber composition according to claim 7,
wherein the aliphatic carboxylic acid in the metal salt (1) of the carboxylic acid is an aliphatic monocarboxylic acid or an aliphatic dicarboxylic acid.

9. The method of producing the rubber composition according to claim 7, wherein the amount of rubber-adhesion promoter is 0.01 to 10 parts by mass with respect to 100 parts by mass of said rubber component.

10. A method of adhering rubber and metal comprising applying a rubber composition comprising a rubber-metal adhesion promoter and a rubber component to a metal component and vulcanizing the rubber to adhere the rubber component and the metal component;
wherein the rubber-metal adhesion promoter comprises:
a compound (2) represented by the following general formula (A):

wherein Z represents a structure selected from the following formulae (z-1) to (z-4);

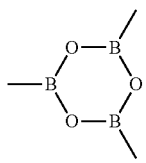

wherein M is bismuth or copper; (RCOO) represents a residue of an aliphatic carboxylic acid having 2 to 25 carbon atoms; and x represents an integer of {(valence of M)−1}.

11. The method of adhering rubber and metal according to claim 10, wherein the metal component is a steel cord.

12. The method of producing the rubber composition according to claim 10, wherein the amount of rubber-adhesion promoter is 0.01 to 10 parts by mass with respect to 100 parts by mass of said rubber component.

13. A method of adhering rubber and metal comprising applying a rubber composition comprising a rubber-metal adhesion promoter and a rubber component to a metal component and vulcanizing the rubber to adhere the rubber component and the metal component;
wherein the rubber-metal adhesion promoter comprises:
a compound (2) represented by the following general formula (A):

wherein Z is a structure represented by formula (z-1),

wherein M represents bismuth, copper, antimony, silver or niobium; (RCOO) represents a residue of an aliphatic carboxylic acid having 2 to 25 carbon atoms; and x represents an integer of {(valence of M)−1}.

14. The method of adhering rubber and metal according to claim 13, wherein the metal component is a steel cord.

15. The method of producing the rubber composition according to claim 13, wherein the amount of rubber-adhesion promoter is 0.01 to 10 parts by mass with respect to 100 parts by mass of said rubber component.

16. A method of adhering rubber and metal comprising applying a rubber composition comprising a rubber-metal adhesion promoter and a rubber component to a metal component and vulcanizing the rubber to adhere the rubber component and the metal component;
wherein the rubber-metal adhesion promoter comprises:
a compound (2) represented by the following general formula (A):

wherein Z represents a structure selected from the following formulae (z-1) to (z-4);

(z-4)

wherein M represents bismuth, copper, antimony, silver or niobium; (RCOO) is a residue of a saturated aliphatic monocarboxylic acid having 2 to 20 carbon atoms; and x represents an integer of {(valence of M)−1}.

17. The method of adhering rubber and metal according to claim 16,
wherein (RCOO) in said compound (2) is a residue of 2-ethylhexanoic acid, a residue of neodecanoic acid, a residue of hexadecanoic acid or a residue of octadecanoic acid.

18. The method of adhering rubber and metal according to claim 16, wherein the metal component is a steel cord.

19. The method of producing the rubber composition according to claim 16, wherein the amount of rubber-adhesion promoter is 0.01 to 10 parts by mass with respect to 100 parts by mass of said rubber component.

* * * * *